US006463394B1

(12) United States Patent
Von Bahr

(10) Patent No.: US 6,463,394 B1
(45) Date of Patent: Oct. 8, 2002

(54) METHOD FOR CALIBRATION AND MEASUREMENT IN A MICRO-DIALYSIS SYSTEM, AND A MICRO-DIALYSIS SYSTEM

(75) Inventor: Pontus Von Bahr, Enskede (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 09/413,024

(22) Filed: Oct. 6, 1999

(30) Foreign Application Priority Data

Oct. 7, 1998 (SE) ............................................ 9803424

(51) Int. Cl.[7] ................................................ G01F 25/00
(52) U.S. Cl. .......................................... 702/100; 700/83
(58) Field of Search ............................ 702/100, 55, 34; 210/87, 646, 96.2, 143, 97, 321.71, 321.79, 645, 739; 73/1.06; 700/83; 600/341, 578, 583, 347; 435/6, 183

(56) References Cited

U.S. PATENT DOCUMENTS 4,123,353 A 10/1978 Håkansson et al.
4,221,567 A 9/1980 Clark et al.
5,247,434 A * 9/1993 Peterson et al. .............. 700/83
5,763,760 A * 6/1998 Gumbrecht et al. ......... 73/1.06
6,027,445 A * 2/2000 Von Bahr ................... 600/309
6,114,176 A * 9/2000 Edgson et al. .............. 436/108

FOREIGN PATENT DOCUMENTS

| | | |
|---|---|---|
| DE | OS 198 21 903 | 1/1999 |
| DE | OS 197 29 491 | 2/1999 |
| EP | 0 715 859 | 6/1996 |
| EP | 0 892 269 | 1/1999 |
| GB | 2 297 383 | 7/1996 |
| WO | WO 92/18832 | 10/1992 |

* cited by examiner

*Primary Examiner*—Marc S. Hoff
*Assistant Examiner*—Mohamed Charioui
(74) *Attorney, Agent, or Firm*—Schiff Hardin & Waite

(57) ABSTRACT

In a method for calibration and measurement of a micro-dialysis system and a micro-dialysis system, one sensor is employed. Measurement times in micro-dialysis tend to be long, since concentration equilibrium at the measurement probe is necessary. The method enables calibration and measurement to be performed with two dialysates with differing analyte contents in order to facilitate measurement with no need to wait for complete equilibrium.

5 Claims, 2 Drawing Sheets

METHOD FOR CALIBRATION AND MEASUREMENT IN A MICRO-DIALYSIS SYSTEM, AND A MICRO-DIALYSIS SYSTEM

BACKGROUND OF THE INVENTION

1. Field of the Invention

The present invention is directed to a method for calibration and measurement in a micro-dialysis system, as well as to a micro-dialysis system wherein the method is implemented.

2. Description of the Prior Art

In micro-dialysis a measurement probe is inserted into the measurement area, usually a part of a patient's body. The measurement probe contains a dialysate that, through a permeable part of the measurement probe, accepts substances diffusing out of the measurement area. The substances can consist of e.g. oxygen ions in blood. The dialysate is subsequently carried to a sensor for measuring the diffusing substance. This provides a measure of a specific parameter in the measurement area, e.g. the blood gas value for oxygen.

One problem in this procedure is to ensure that the sensor measures a relatively correct value. If the sensor does not measure a direct value, it should be possible to at least calculate the correct value.

In principle, two factors have a predominant impact on sensor accuracy: the measurement probe's recovery ability and the sensor's signal drift.

Recovery ability R is defined as $$R = \frac{C_{dialysate}}{C_{measurement\ area}}$$

where C stands for the concentration of the diffusing substance (in the dialysate and measurement area respectively).

Recovery ability depends, in turn, on factors such as temperature, the material the measurement probe is made of, the flow of dialysate and convection around the measurement probe. Several of these factors vary with time, and the system must operate very slowly, or recovery must be monitored in some way, to assure 100% recovery between each measurement. If recovery is monitored, a calculation can be made to compensate for measurements made before 100% recovery has taken place.

SUMMARY OF THE INVENTION

An object of the present invention is to provide a method for micro-dialysis which solves the aforementioned problems.

Another object of the invention is to provide a micro-dialysis system capable of performing measurements more rapidly and accurately than known micro-dialysis systems.

The above object is achieved in accordance with the principles of the present invention in a method for calibration and measurement of a micro-dialysis system, and a micro-dialysis system wherein the method is implemented, employing a sensor wherein calibration and measurement are performed with two dialysates respectively containing different analytes.

A more effective analysis method can be employed when two dialysates, with differing analyte contents with respect to the parameter to be identified, are used. The two dialysates are employed so that calibration and measurement are performed with one dialysate at a time. The first dialysate is used at appropriate intervals, preferably for every second calibration and measurement. The second dialysate is used for the remaining calibrations and measurements.

100% recovery is then no longer necessary, since two-paint calibration of the sensor becomes possible. This is accomplished by utilization of the three most recent sensor readings for determining a measurement value, i.e., two calibrations and the actual measurement.

The micro-dialysis system is devised to enable two dialysates to be used alternately in a suitable fashion for performing the method described above.

DESCRIPTION OF THE PREFERRED EMBODIMENTS

In micro-dialysis, a measurement probe is inserted into a measurement field, as a rule by invasive introduction into a patient. A typical example of this is insertion into a patient's vein or artery for the purpose of measuring blood gases. The measurement probe is filled with a dialysate. Gas molecules, e.g. oxygen, in the measurement probe's surroundings diffuse into the measurement probe. When equilibrium has been reached, the concentration of the gas molecules in the measurement area can be measured by measuring the concentration in the dialysate. Measurement is performed by a sensor.

As is the case with most types of measurement equipment, the micro-dialysis system is subject to signal drift which can lead to erroneous measurement results. Two primary factors for this in micro-dialysis systems are signal drift in the sensor, and the measurement probe's recovery time.

Signal drift in the sensor can be remedied with recurrent calibration during operations. Calibration must then be performed at a known concentration.

Recovery time for the probe is more complex. In concrete terms, this means that concentration equilibrium must be complete before the dialysate can be sent from the probe to the sensor. A number of factors affect this. The temperature, the material the measurement probe is made of, the flow of dialysate, convection in the measurement area etc. A number of these factors also change over time. This means that the micro-dialysis system must normally operate slowly to keep measurement, results from being compromised.

This problem is solved with the present invention by utilization of two dialysates with different analyte contents. These dialysates are employed in achieving two point calibration of the sensor.

The dialysates are utilized alternately, i.e. first calibration and measurement with one dialysate and then calibration and measurement with the other dialysate. When the last two calibrations are utilized with the latest measurement, correct measurement values can be obtained with no need to take the measurement probe's recovery time into account.

Figure 1:
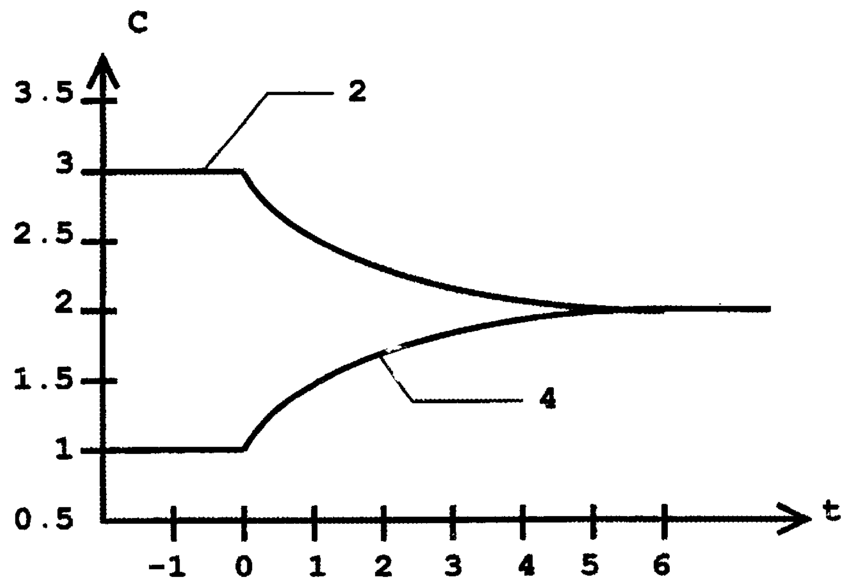
FIG. 1 is a diagram illustrating the course of recovery for two dialysates.

FIG. 1 is a diagram showing concentration curves for a first dialysate 2 and a second dialysate 4. The y axis shows the concentration, and the x axis shows the time in minutes. With the designation $C_1$ for the concentration of the first dialysate, $C_2$ for the concentration of the second dialysate and $C_x$ for the concentration in the measurement area, the following relationships can be established for the concentration's variation in the measurement probe:

$$C_{1X}=C_1+(C_x-C_1)(1-e^{-\alpha T}) \quad [1]$$

$$C_{2X}=C_2+(C_x-C_2)(1-e^{-\alpha T}) \quad [2]$$

wherein α is a diffusion constant and t designates time. At time zero the dialysates 2, 4 have initial concentrations of $C_1$ and $C_2$ respectively. The concentration then decreases (for the first dialysate, corresponding to $C_{1X}$) and increases (for the second dialysate, corresponding to $C_{2X}$) exponentially with time, achieving after about 5 minutes the concentration $C_x$ (at which equilibrium prevails) of the surroundings (measurement area).

It should be emphasized that the diagram shows a concrete example of the variation in concentration. The time elapsing until equilibrium occurs can therefore vary considerably, depending on the circumstances.

A reasonable assumption is that the sensor exhibits, or can be made to display, a linear correlation between the concentration and output voltage. When calibrations are at least performed with the same dialysate flow, the corresponding chronological course will take place in the measurement probe. It is also reasonable to expect the time constant, temperature and other factors not to change drastically. They can therefore be viewed as constants over at least two calibration procedures.

The equations [1] and [2] then only contain two unknowns, viz, the diffusion constant a and the equilibrium concentration $C_x$. These equations can them be merged to form the following relationship:

$$C_x = \frac{C_1(C_{2x} - C_2) - C_2(C_{1x} - C_1)}{C_{2x} - C_2 - C_{1x} + C_1} \quad (3)$$

The output signals from the sensor are voltages and can be designated $U_{1x}$ and $U_{2x}$ for unknown concentrations ($U_1$ is obtained for the first dialysate at the concentration $C_1$ and $U_2$ for $C_2$). With the aforementioned assumptions that the sensor displays a linear correlation and that the parameters can be regarded as constants over short intervals, the following transfer function is obtained for the sensor's output signal:

$$U = U_1 + \frac{U_2 - U_1}{C_2 - C_1}(C - C_1) \quad (4)$$

With this transfer function, equations [1] and [2] can be expressed as:

$$C_{1x} = C_1 + \frac{C_2 - C_1}{U_2 - U_1}(U_{1x} - U_1) \quad (5)$$

$$C_{2x} = C_2 + \frac{C_2 - C_1}{U_2 - U_1}(U_{2x} - U_1) \quad (6)$$

Utilization of the equations [3], [5] and [6] makes it possible to calculate the unknown concentration $C_x$ of a sample from the known concentrations $C_1$, $C_2$ in the dialysate, the two calibrations $U_1$, $U_2$ and the two measurements $U_{1x}$, $U_{2x}$.

The system therefore automatically compensates for all slow signal drifting.

Constant utilization of preceding measurements results in a faster system, relatively speaking. (Two measurements and two calibrations are only required initially before calculation can start as above.)

Figure 2:
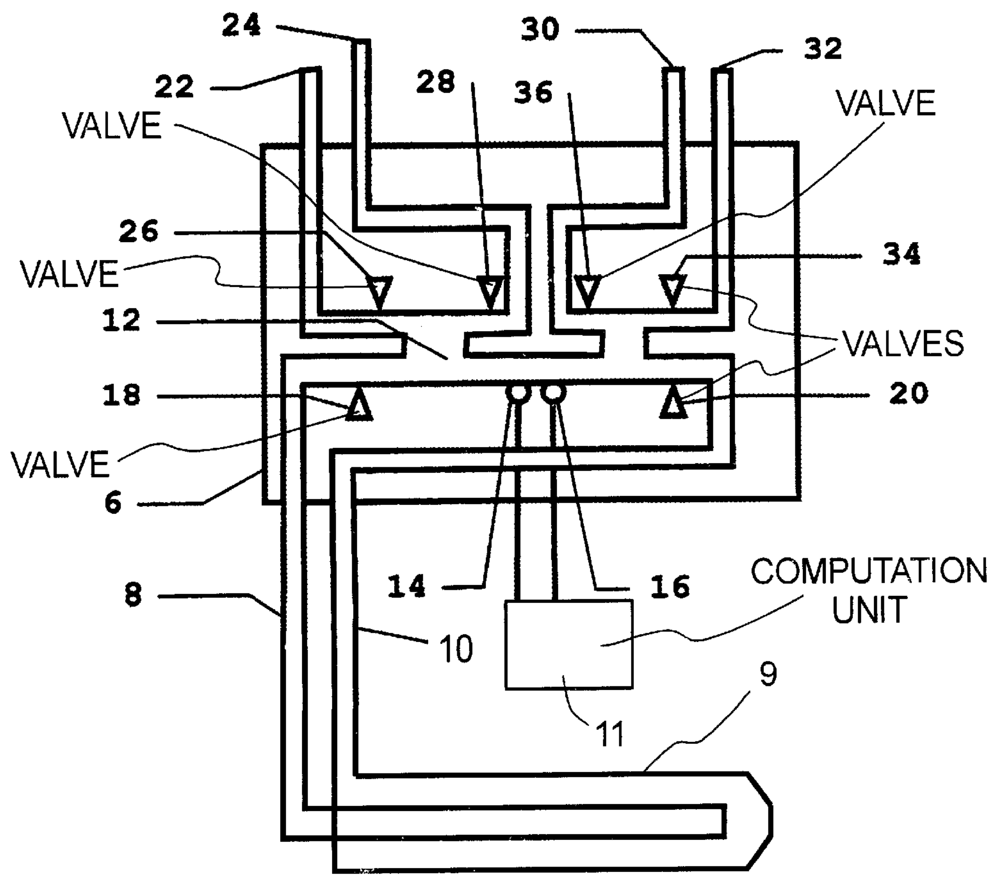
FIG. 2 is a schematic depiction of a first embodiment of a measurement cassette in a micro-dialysis system according to the invention.

FIG. 2 schematically depicts a measurement cassette 6 in a micro-dialysis system in which measurement is performed in the measurement cassette 6.

A dialysate from a measurement probe 9 enters the measurement cassette 6 for measurement through a first inlet 8. At the same time, dialysate is sent to the measurement probe 9 through a first outlet 10. The incoming dialysate proceeds to a test chamber 12 and comes into contact with a first sensor 14 and a second sensor 16, for example, for determination of the concentration of oxygen ions in the dialysate. The sensors 14, 16 supply signals to a computation unit 11.

The flow to and from the measurement probe can be stopped with a first valve 18 and a second valve 20. The measurement probe should be devised to enable dialysate to flow in both directions, i.e. not only in through the inlet 8 and out through the outlet 10, but the reverse as well.

A first calibration dialysate can be fed into the measurement chamber 12, through a second inlet 22, for calibration of the sensors 14, 16 at a first specific concentration. The sensors 14,16 supply signals to the computation unit 11. The first calibration dialysate can be conducted out of the measurement cassette 6 through a second outlet 24.

The flow of the first calibration dialysate can be stopped with a third valve 26 and a fourth valve 28.

In the corresponding fashion, a second calibration dialysate can be fed into the measurement chamber 12, through a third inlet 30, for calibration of the sensors 14,16 at a second specific concentration. The sensors 14, 16 supply signals to the computation unit 11. The second calibration dialysate can be carried out of the measurement cassette 6 through a third outlet 32.

The flow of the second calibration dialysate can be stopped with a fifth valve 34 and a sixth valve 36.

During operation the first calibration dialysate is first conducted to the measurement chamber 12 for a first calibration of the sensors 14,16 in the computation unit 11. An amount of the first calibration dialysate, which is also sufficient to fill the measurement probe, must also be supplied. The sensors 14, 16 thus are calibrated.

After a certain amount of time, the first calibration dialysate can be recovered from the measurement probe and returned to the cassette 6 via the inlet 8 for measurement of its (now) unknown concentration.

In a corresponding manner, the second calibration dialysate is then conducted into the measurement chamber 12 for a second calibration in the computation unit 11 and subsequently into the measurement probe and back into the cassette 6 for a second measurement.

The determination procedure has already been described above.

Figure 3:
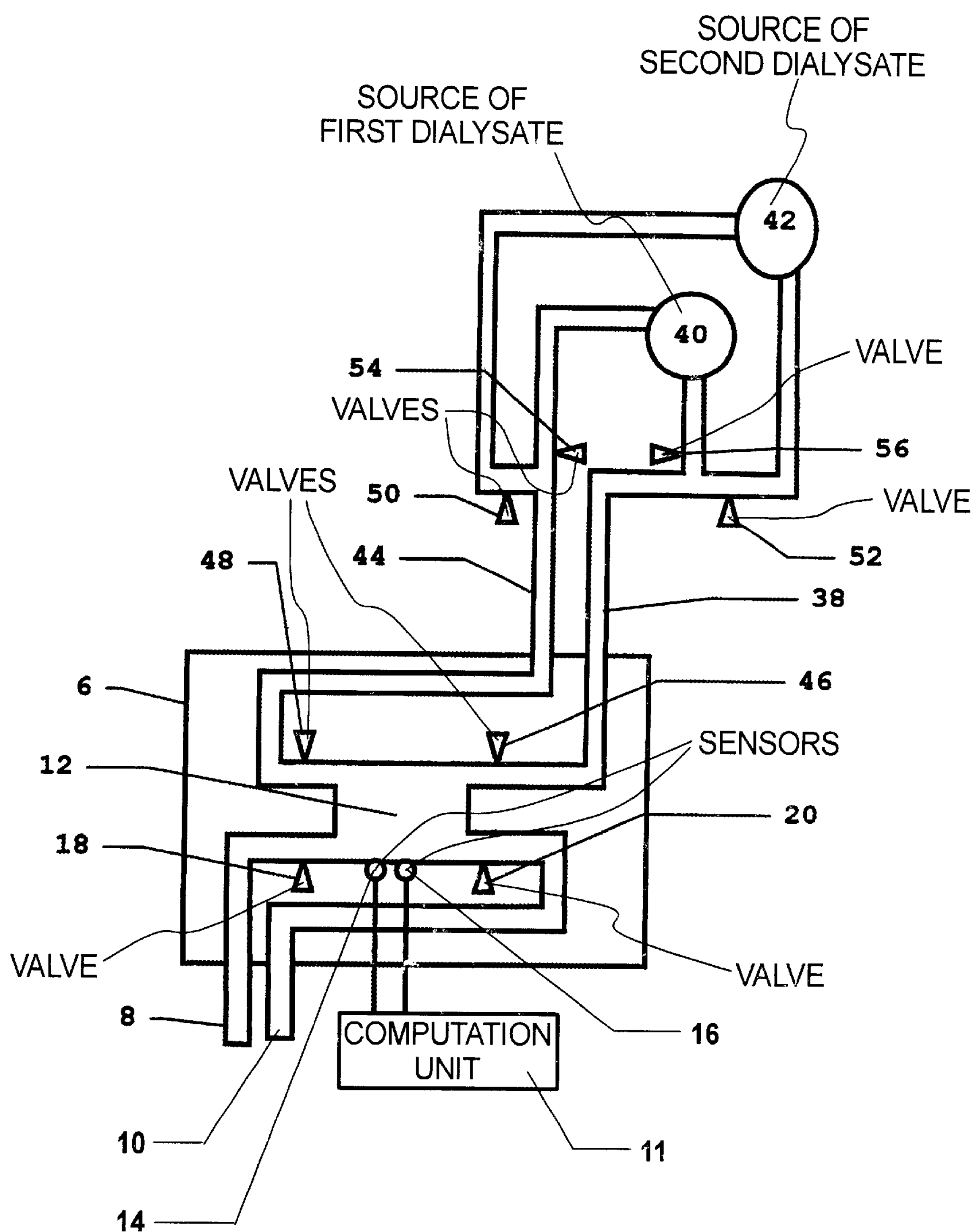
FIG. 3 is a schematic depiction of a second embodiment of a 30 measurement cassette in a micro-dialysis system according to the invention.

FIG. 3 shows an alternative design for the measurement cassette 6 in a second embodiment. The same designations are used for identical components. The measurement cassette 6 comprises a first inlet 8 and a first outlet 10 which leads to a measurement chamber 12 in the measurement cassette 6. Sensors 14, 16 are arranged in the measurement chamber to measure concentration. A first valve 18 and a second valve 20 can stop flow in the measurement probe.

A first calibration dialysate from a first source 40 or a second calibration dialysate from a second source 42 can be added through a second inlet 38. Dialysate is returned to the respective source 40, 42 through a second outlet 44.

Switching to the respective dialysate and control of flow through the measurement chamber 12 is by means of a third valve 46, a fourth valve 48, a fifth valve 50, a sixth valve 52, a seventh valve 54 and an eighth valve 56.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for measurement in a micro-dialysis system, comprising:

supplying a first dialysate, containing an analyte at a first concentration, for exposure to a substance to be measured;

performing a measurement on said first dialysate before and after exposure to said substance to be measured to obtain a first calibration reading and a first measurement reading respectively;

supplying a second dialysate, containing an analyte at a second concentration, for exposure to said substance to be measured;

performing a measurement on said second dialysate before and after exposure to said substance to be measured to obtain a second calibration reading and a second measurement reading respectively; and determining said concentration of said substance from said first and second concentrations, said first and second calibration readings, and said first and second measurement readings.

2. A method as claimed in claim 1 comprising supplying said first and second dialysates to said substance in a predetermined pattern and preceding each measurement reading with no more than one of said calibration readings respectively obtained using one of said dialysates.

3. A method as claimed in claim 1 comprising successively alternatingly supplying said first dialysate and said second dialysate to said substance.

4. A method for measurement in a micro-dialysis system, comprising:

providing a measurement probe;

providing a sensor, connected to said measurement probe, for conducting a measurement;

supplying a first dialysate, containing an analyte at a first concentration, to said sensor and to said measurement probe;

obtaining a first calibration reading by measuring a concentration of said first dialysate in said sensor while exposing said first dialysate in said measurement probe to a substance to be measured;

transferring said first dialysate in said measurement probe, after exposure to said substance, to said sensor and measuring a concentration of said substance in said first dialysate to obtain a first measurement reading from said sensor;

supplying a second dialysate, containing an analyte at a second concentration, to said sensor and to said measurement probe;

obtaining a second calibration reading by measuring a concentration of said second dialysate in said sensor while exposing said second dialysate in said measurement probe to said substance;

transferring said second dialysate in said measurement probe, after exposure to said substance, to said sensor and measuring a concentration of said substance in said first dialysate to obtain a second measurement reading from said sensor; and determining said concentration of said substance from said first and second concentrations, said first and second calibration readings and said first and second measurement readings.

5. A micro-dialysis system comprising:

means for supplying a first dialysate, containing an analyte at a first concentration, for exposure to a substance to be measured;

means for performing a measurement on said first dialysate before and after exposure to said substance to be measured to obtain a first calibration reading and a first measurement reading respectively;

means for supplying a second dialysate, containing an analyte at a second concentration, for exposure to said substance to be measured;

means for performing a measurement on said second dialysate before and after exposure to said substance to be measured to obtain a second calibration reading and a second measurement reading respectively; and means for determining said concentration of said substance from said first and second concentrations, said first and second calibration readings and said first and second measurement readings.

* * * * *